United States Patent [19]

Huebner et al.

[11] Patent Number: 5,612,037
[45] Date of Patent: Mar. 18, 1997

[54] INFLUENZA VIRUS SUBUNIT CONJUGATES

[75] Inventors: Robert C. Huebner, Bartonsville; Maurice W. Harmon, Tannersville, both of Pa.

[73] Assignee: Connaught Laboratories, Inc., Swiftwater, Pa.

[21] Appl. No.: 280,463

[22] Filed: Jul. 26, 1994

[51] Int. Cl.$^6$ ...................... A61K 39/145; A61K 39/385
[52] U.S. Cl. .................... 424/194.1; 424/193.1; 424/196.11; 424/209.1; 424/210.1
[58] Field of Search .................... 424/209.1, 210.1, 424/193.1, 194.1, 196.11

[56] References Cited

U.S. PATENT DOCUMENTS

| 4,762,913 | 8/1988 | Stevens | 530/345 |
|---|---|---|---|
| 5,292,506 | 3/1994 | Oki et al. | 424/450 |
| 5,354,554 | 10/1994 | Rhind | 424/1.49 |

FOREIGN PATENT DOCUMENTS 0270295  6/1988  European Pat. Off. .

OTHER PUBLICATIONS

Madoff, D.H. and Lenard, J. (1982) Cell 28:821–828.
Neimann, H. and Klenk, H.D. (1981) J. Molecular Biology 153:991–1010.
Johnson, D.C. and spear, P.G. (1983) Cell 32:987–997.
Veit, M., Schmidt, M.F.G. and Rott, R. (1989) Virology 168:173–176.
Hardwick, J.M. et al. (1986) J. Cell Biology 103:829–838.
Schmidt, M.f.G. and Schlesinger, M.J. (1979) Cell 17:813–819.
Hiller, G. and Weber, K. (1985) J. Virology 55:651–659.
Schmidt, M.F.G., Brecha, M. and Schlesinger, M.J. (1979) Proceedings of the National Academy of Science, USA 76:1687–1691.
Hancock, J.F. et al. (1989) Cell 57:1167–1177.
Jing, S. and Trowbridge I.S. (1987) EMBO J. 6:327–331.
Segruc, R.J., Belshe, R.B., and Hay, A.J. (1990) Virology 179:51–56.
Schmidt, M.F.G. and Lambrecht, B., (1985) J. gen. Virol. 66:2635–2647.
Veit, M., Herrier, G., Schmidt, M.F.G., Rott, R. and Klenk. H–D, (1990) Virology 177:807–811.

Primary Examiner—Mindy Fleisher
Assistant Examiner—Terry A. McKelvey
Attorney, Agent, or Firm—Curtis, Morris & Safford, P.C.

[57] ABSTRACT

Conjugates of HA protein of influenza virus suitable for formulation as a vaccine for obtaining a strong immune response to the HA protein are formed by separating whole HA protein from the influenza virus by detergent extraction or by providing whole HA protein by recombinant procedure, treating the HA protein with hydroxylamine to form free sulfhydryl groups in the cytoplasmic domain of the protein, and cross-linking the free sulfhydryl group-containing HA protein to itself using a bis-maleimide linker or to a maleimide-modified diphtheria toxoid, tetanus toxoid or influenza NP protein or other carrier molecule. The procedure is applicable to other proteins which can be separated from a cellular material, such as a virus, and which contain thioester bonds convertible to sulfhydryl groups.

9 Claims, No Drawings

INFLUENZA VIRUS SUBUNIT CONJUGATES

FIELD OF INVENTION

The present invention relates to conjugation of influenza virus hemagglutinin (HA) to carrier molecules and the use of such conjugates in immunogenic compositions, particularly vaccines for human administration.

BACKGROUND TO THE INVENTION

Whole virus vaccines administered to the body elicit an immune response by the formation of antibodies to the viral antigen. In the case of the influenza virus, it is known that the influenza HA protein is the target of virus neutralizing antibodies for this virus. One commercially-available whole virus vaccine is a split virus vaccine, obtained by treating inactivated virus with detergent, is sold under the trade-mark FLUZONE® by Connaught Laboratories, Inc.

The trend with respect to vaccines is away from whole virus materials and towards more purified materials, which generally are smaller and well defined. The influenza HA antigen has been isolated but the specific subunit materials are only weakly immunogenic and are incapable of inducing a sufficiently high immune response to be effective in many classes of individuals.

There was previously described in published EP 87-310377, assigned to the assignee hereof, the covalent bonding of HA to diphtheria toxoid. As described therein, the HA was removed from the whole virus by bromelain cleavage and the resulting HA-subunit was covalently bonded to diphtheria toxoid using a heterobifunctional cross-linker of the maleimide-N-hydroxy-succinimide ester type, particularly MCS (maleimido-caproic acid-N-hydroxysuccinimide ester). In preparing the HA-D conjugate, a sulfhydryl group first is introduced to the HA-subunit by treatment with SATA (N-succinimidyl-S-acetylthioacetic acid), the N-hydroxysuccinimide ester is reacted with amino groups on the diphtheria toxoid (DT), and then the maleimide component is reacted with the free sulfhydryl groups introduced to the HA antigen to link the HA and DT molecules to form the HA-D conjugate.

While the results which were obtained in human efficacy trials showed the HA-D conjugate vaccine to produce a greater immune response than the HA subunit vaccine alone, the HA-D conjugate was not more effective in producing an immune response in humans, when compared to whole influenza virus vaccine.

SUMMARY OF INVENTION

We now have developed an improved procedure which permits the provision of HA-conjugates and conjugates of other viral subunit proteins which are more effective immunogens than the conjugates previously described. In the present invention, separation of the HA subunit from the whole virus is effected in a manner different from that previously described and enables the improved result to be obtained.

Our approach has been to provide a procedure which is designed to leave intact all the immunologically important sites on the HA protein. The procedure previously used, namely bromelain cleavage and derivatization of amine groups for the conjugation process may have produced modification of such sites, leading to the results which were observed, i.e. lack of greater effectiveness when compared to whole influenza virus vaccine.

Accordingly, in one aspect of the present invention, there is provided a method of forming a conjugate of an HA protein of influenza virus. The first step of the method is to effect separation of whole HA protein from influenza virus by detergent extraction. In the prior procedure, the HA protein was cleaved from the virus by bromelain. The effect of the detergent extraction procedure employed herein is to include the transmembrane and endodomains in the separated HA protein, which is not the case with bromelain cleavage, where such elements remain with the viral material. In addition to extraction of the HA protein from the virus, the HA protein also may be formed recombinantly for further processing.

The separated whole HA protein then is treated with hydroxylamine or other convenient chemical to generate reactive sulfhydryl groups in the endodomain by converting thioester bonds in the endodomain. In the prior procedure, sulfhydryl groups were introduced to the bromelain-cleaved subunit by thiolation. It is believed that this difference in HA subunits obtained by the two different extraction procedures accounts for the different properties observed.

The resulting free sulfhydryl-containing HA protein then is cross-linked to a carrier molecule capable of eliciting a potentiated immune response to the HA protein. Such cross-linking may be effected either to itself using a bis-maleimide linker or to maleimide-modified diphtheria toxoid, tetanus toxoid or influenza NP protein to form a conjugate. The resulting HA-conjugate may be formulated as a vaccine against influenza.

GENERAL DESCRIPTION OF INVENTION

As noted above, the present invention is directed to obtaining a potentiated immune response to influenza virus HA protein by conjugation. One important aspect of the procedure is extracting or recombinantly forming and conjugating the whole HA protein from the influenza virus in a manner which leaves all the immunologically important sites on the HA protein intact. The invention is applicable to the HA protein from a variety of strains of the influenza virus, including type A and type B influenza.

The success achieved herein with respect to the HA protein is indicative that the procedure is applicable to other weakly immunogenic proteins isolated from whole virus material or formed by recombinant procedures in which free sulfhydryl groups may be generated in the endodomain. Among the other weakly immunogenic proteins to which the procedure of the present invention may be employed are the G1 and G2 proteins of LaCrosse virus (ref. 1, a list of references appears at the end of the disclosure), the E2 protein of mouse hepatitis virus (ref. 2), the gE protein of herpes simplex virus type 1 (ref. 3), the F and HN protein of Newcastle disease virus (ref. 4), the gp35 protein of Rous sarcoma virus (ref. 5), protein G of vesicular stomatitis virus (ref. 6), the P37 protein of vaccina virus (ref. 7), the E1 and E2 proteins of Sindbis virus (ref. 8), the H-ras protein (ref. 9), influenza M2 protein (ref. 11) and the human transferrin receptor (ref. 10). Accordingly, in a broad aspect of the present invention, there is provided a method of forming a conjugate of a protein normally associated with cellular material either by extraction from the cellular material or by recombinant means, which comprises separating a protein having at least one thioester group in a terminal region thereof from the cellular material, treating the separated protein to form at least one free sulfhydryl group from the at least one thioester group, and cross-linking the sulfhydryl group-containing protein to a carrier molecule by bonding through the at least one free sulfhydryl group.

The procedure of the invention is described hereafter with respect to the HA protein but it will be understood that equivalent procedures can be used for these other proteins for forming conjugates thereof.

The first step in the conjugation procedure is to isolate the whole HA protein from the influenza virus under non-denaturing conditions. Such procedure may involve detergent extraction using octyl-β-glucoside, sodium cholate or other non-denaturing detergents. Alternatively, the HA protein may be formed recombinantly by expression from a suitable expression system.

Following extraction of the whole HA protein with detergent or formation by recombinant procedure, the HA protein is treated with hydroxylamine, thiol reducing agents or by acid or base hydrolysis to generate free sulfhydryl groups in the endodomain of the protein, by breaking thioester bonds in the endodomain to form free sulfhydryl groups.

The free sulfhydryl-containing HA protein then is conjugated to another molecule through chemical bonding through the free sulfhydryl groups. Such conjugation may be by way of conjugation of the HA protein to itself by use of a suitable bis-maleimide compound, such as one of the formula:

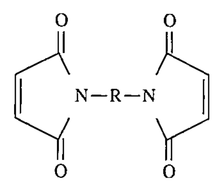

where R is a hydrocarbon radical, such as hexane.

Alternatively, the conjugation of the HA protein may be to a maleimide-modified carrier protein, such as diphtheria toxoid, tetanus toxoid or influenza (NP) protein or to a carbohydrate, such as alginic acid, dextran or polyethylene glycol. Such maleimide-modified carrier molecules may be formed by reaction of the carrier molecule with a heterobifunctional cross-linker of the maleimide-N-hydroxysuccinimide ester type, as described in the above-mentioned prior art.

Such compounds may have the formula:

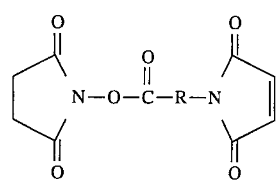

where R is any convenient acid residue and may include an optionally-substituted phenylene group, cycloalkylene group or alkylene group from 1 to 12 carbon atoms, preferably 5 to 12 carbon atoms. Examples of such bifunctional esters include maleimido-caproic-N-hydroxysuccinimide ester (MCS), maleimido-benzoyl-N-hydroxysuccinimide ester (MBS), maleimido-benzoylsul-fosuccinimide ester (sulfo-MBS), succinimidyl-4-(N-maleimidomethyl) cyclohexane-1-carboxylate (SMCC), succinimidyl-4-(p-maleimido-phenyl)butyrate (SMPP), sulfosuccinimidyl-4-(N-maleimidomethyl)cyclohexane-1-carboxylate (sulfo-SMCC) and sulfosuccinimidyl-4-(p-maleimidophenyl) butyrate (sulfo-SMPP).

The N-hydroxy-succinimide ester moiety reacts with the amine groups of the carrier protein leaving the maleimide moiety free to react with the sulfhydryl groups on the antigen to form the cross-linked material.

The conjugate molecules so produced may be purified and employed in immunogenic compositions as vaccine materials to elicit, upon administration to a host, an immune response to the HA protein which is potentiated in comparison to HA alone and, in some instances, exceeds the response to commercial split influenza vaccine.

The immunogenic compositions containing such conjugate molecules may be prepared as injectables, as liquid solutions or emulsions. The conjugate molecules may be mixed with physiologically-acceptable carriers which are compatible therewith. These carriers may include water, saline, dextran, glycerol, ethanol and combinations thereof. The composition may further contain auxiliary substances, such as wetting or emulsifying agents or pH buffering agents. Vaccines may be administered by injection, subcutaneously or intramuscularly, or may be delivered in a manner to evoke an immune response at mucosal surfaces.

The immunogenic compositions are administered in a manner compatible with the dosage formulation, and in such amount as to be therapeutically effective, protective or immunogenic. The quantity of conjugate to be administered depends on the subject to be immunized, including the capacity of the immune system of the subject to synthesize antibodies and, if needed, to produce a cell-mediated immune response. Precise amounts of conjugate to be administered depends on the judgement of the practitioner. However, suitable dosage ranges are readily determinable by those skilled in the art and may be in the order of micrograms to milligrams. Suitable regimes for initial administration and booster doses are also variable, but may include an initial administration followed by subsequent administrations. The dosage of the vaccine may also depend on the route of administration and will vary accordingly to the size of the host.

The immunogenic compositions comprising the novel conjugates provided herein are useful for the generation of antigen-specific antibodies that are useful in the specific identification of that antigen in an immunoassay. Such immunoassays include enzyme-linked immunosorbent assays (ELISA), RIAs and other non-enzyme linked antibody binding assays or procedures known in the art.

EXAMPLES

Example 1:

This Example illustrates the preparation of influenza virus subunit.

Influenza virus (A/Taiwan and A/Beijing) was pelleted by centrifugation, the supernatant was removed and the pellet was resuspended in a small amount of phosphate buffered saline (PBS). PBS containing 10 wt. % of the detergent octyl-β-glucoside, was added to bring the final detergent concentration to 2 wt. %. The material was gently mixed and incubated at 37° C. for one hour. The virus core and debris was removed by centrifugation. The supernatant from the centrifugation comprised HA subunit separated from the virus by detergent extraction.

Example 2:

This Example illustrates the preparation of a HA-BM-H:HA conjugates.

The detergent-extracted HA, prepared as described in Example 1, then was mixed with 5M hydroxylamine, pH 7.2, 2mM EDTA at a ratio of 4:1 to produce terminal sulfhydryl groups in the HA molecule. A three-fold molar excess of bismaleimidohexane (BMH, 5 mg/ml in dimethylsulfoxide) to HA monomer was added. The reaction was incubated for 30 minutes at room temperature. The BMH-modified HA then was mixed with an excess of hydroxylamine-treated HA. A/Taiwan HA was used to produce materials with BMH-modified to unmodified HA ratios of 1:2, 1:4, 1:8 and 1:16. A/Beijing HA was used to make materials with ratios of 1:2, 1:4 and 1:8. These reactions were incubated at room temperature for several hours. The final product was purified by ultrafiltration through a 300,000 nominal molecular weight cut-off membrane.

Example 3:

This Example illustrates the preparation of HA-carrier antigen conjugate.

Carrier antigens were first modified using sulfo-SMCC. Carrier protein concentrations were determined using a micro-BCA protein assay. In this regard, toxoid carrier proteins in phosphate buffered saline at pH 7.3 were incubated with a 15-fold molar excess of sulfo-SMCC for two hours at room temperature. NP protein was incubated with a 25-fold excess of sulfo-SMCC for two hours at room temperature in phosphate buffered saline containing one molar sodium chloride. Alginic acid was modified with adipic acid dihydrazide in the presence of 1-(3-dimethyl amino propyl)-3-ethylcarbodiimide at pH 5.0 for 120 minutes at room temperature. Following adipic and modification, this material was dialyzed against phosphate buffered saline to remove the unreacted hydrazide. Hydrazide modified alginic acid was incubated with a 2-fold molar excess of sulfo-SMCC for 270 minutes at room temperature in phosphate buffered saline at pH 7.3.

Unreacted sulfo-SMCC cross-linker was removed by gel filtration through a fast desalting column (Pharmacia LKB Biotechnology, Piscataway, N.J.). The maleimide content of the modified carrier was determined using 5'5-dithio-bis-(2-nitrobenzoic acid). The modified carrier then was linked to hydroxylamine-treated HA, prepared as described in Example 2, at a ratio of one maleimide per free sulfhydryl. The cross-linking reaction and purification of conjugated material was carried out as described in Example 2.

Example 4:

This Example shows the immune response obtained in mice to certain of the conjugates (A/Taiwan).

A/Taiwan HA-BMH: HA conjugates and HA-carbohydrate conjugate were tested for immunogenicity and efficacy in mice. Mice were immunized at 0 and 3 weeks and bled or challenged with live A/Taiwan virus at 5 weeks. HA-HA conjugate and HA-carbohydrate vaccines were compared to a commercial split influenza vaccine (Fluzone®) and placebo, at various vaccine dosages. The results obtained are set forth in the following Table I:

TABLE I

Immunogenicity and Efficacy of HA-HA and HA-Carbohydrate Conjugates (FM-16)

| Antigen | Dose (ng) | Lung Titer ($10^x$) | HI-Antibody* | Neut-Antibody* | Mortality(%) |
|---|---|---|---|---|---|
| HA-Alginic Acid, LV# | 250 | 0.70 | 40 | 60 | ND |
|  | 50 | 3.67 | 40 | 18 | 1/6 (17) |
|  | 5 | 5.52 | 5 | 5 | 2/6 (33) |
| HA-BMH: HA (1:1) | 250 | 3.98 | 35 | 30 | ND |
|  | 50 | 4.78 | 7 | 5 | 0/6 |
|  | 5 | 5.08 | 5 | 5 | 2/6 (33) |
| HA-BMH: HA (1:4) | 250 | <0.7 | 187 | 482 | ND |
|  | 50 | 2.38 | 18 | 18 | 0/6 |
|  | 5 | 4.71 | 5 | 5 | 3/6 (50) |
| Fluzone® | 250 | 4.30 | 53 | 42 | ND |
|  | 50 | 4.52 | 5 | 5 | 0/6 |
|  | 5 | 5.00 | 7 | 5 | 0/6 |
| PBS | — | 5.58 | 5 | 5 | 6/6 (100) |

Low Viscosity Alginic Acid.
*Mice immunized at 0 and 3 weeks and bled at 5 weeks.
ND Not Done.

As may be seen from this data, self-conjugates made using BMH can block the replication of virus in the lungs of mice and generate higher antibody titers than the conventional vaccine.

Example 5:

This Example shows the immune response in mice to other conjugates (A/Taiwan).

Conjugates of HA with DT, TT and NP also were tested for immunogenicity and efficacy in mice following the same protocol as Example 4 and compared to split vaccine (Fluzone) and placebo (PBS). The results obtained are set forth in the following Table II:

TABLE II

Comparison of Three Conjugates (FM-17)

| Antigen | Dose (ng) | HI-5 Wk | Neut-5 Wk | Lung Titer ($10^x$) | Mortality | (%) |
|---|---|---|---|---|---|---|
| HA-DT | 250 | 120 | 123 | <0.7 | N/D | — |
|  | 50 | 42 | 22 | 4.08 | 0/6 | 0 |
|  | 5 | 5 | 5 | 4.80 | 1/6 | 16.7 |
| HA-TT | 250 | 93 | 187 | <0.7 | N/D | — |
|  | 50 | 80 | 133 | 4.46 | 1/6 | 16.7 |
|  | 5 | 63 | 58 | 4.99 | 0/6 | 0 |
| HA-NP | 250 | 53 | 137 | 3.91 | N/D | — |
|  | 50 | 67 | 63 | 4.40 | 0/6 | 0 |
|  | 5 | 7 | 5 | 4.79 | 1/6 | 16.7 |
| Fluzone® | 250 | 147 | 47 | 3.88 | N/D | — |
|  | 50 | 107 | 120 | 3.32 | 0/6 | 0 |
|  | 5 | 17 | 12 | 4.92 | 0/6 | 0 |
| PBS | — | 5 | 5 | 5.41 | 4/6 | 66.7 |

N/D = Not Done.

As may be seen from this data, the toxoid conjugates are able to block replication of virus in the lungs of mice. The tetanus conjugate appears to be slightly better at blocking replication.

Example 6:

This Example shows the immune response obtained in guinea pigs to certain of the conjugate (A/Taiwan).

Antibody assays in guinea pigs gave a different set of results than reported in Examples 4 and 5 for mice. In this Example, the guinea pigs were immunized at week 0 and boosted at 2 weeks and 4 weeks. Bleeds were taken at 5 and 7 weeks and tested.

The self-conjugates and tetanus toxoid conjugate gave results similar to the whole cell vaccine. The diphtheria conjugate was able to generate significantly-higher antibody titers. The conjugate made with the NP protein generated a lower antibody response that continued to rise over the course of the test period and, by the end of the test, a significantly higher antibody response had been generated. The results obtained are set forth in Table III:

TABLE III

Guinea Pig Testing of A/Taiwan Conjugates

| Antigen | Dose (µg) | HAI 3 week | HAI 5 week | HAI 7 week | HAI 9 week |
|---|---|---|---|---|---|
| HA-Alginic acid | 0.5 | 48 | 279 | 1114 | 105 |
|  | 5 | 61 | 184 | 557 | 211 |
| HA-BMH-HA (1:4) | 0.5 | 92 | 28 | 640 | 95 |
|  | 5 | 40 | 367 | 557 | 243 |
| HA-DT | 0.5 | 61 | 2560 | 1810 | 905 |
|  | 5 | 61 | 1470 | 735 | 485 |
| HA-TT | 0.5 | 13 | 368 | 422 | 61 |
|  | 5 | 30 | 422 | 557 | 61 |
| HA-NP | 0.5 | 46 | 320 | 368 | 844 |
|  | 5 | 40 | 61 | 557 | 640 |
| Fluzone ® | 0.5 | 70 | 11 | 844 | 279 |
|  | 5 | 61 | 184 | 640 | 7 |

Example 7:

The procedure of Examples 1 and 2 was used to prepare an A/Beijing HA-BMH: HA conjugate which was tested as described in Example 4. The results obtained, which mimic those obtained with the A/Taiwan strain, are set forth in the following Table IV:

TABLE IV

Intramuscular Immunizations with A/Beijing HA-BMH-HA Conjugates (FM-22)

| Antigen | Dose (ng) | HI- 5 Wk | HI- 7 Wk | Lung Titer ($10^x$) |
|---|---|---|---|---|
| HA-BMH:HA (1:2) | 250 | 403 | 453 | 1.88 |
|  | 50 | 508 | 320 | 2.93 |
|  | 5 | 50 | 101 | 3.63 |
| HA-BMH:HA (1:4) | 250 | 806 | 508 | <0.70 |
|  | 50 | 202 | 202 | <0.70 |
|  | 5 | 160 | 127 | <0.70 |
| HA-BMH:HA (1:8) | 250 | 508 | 403 | <0.70 |
|  | 50 | 199 | 254 | <0.70 |
|  | 5 | 254 | 80 | 3.43 |
| Fluzone ® | 250 | 320 | 202 | 1.78 |
|  | 50 | 63 | 80 | 2.98 |
|  | 5 | 63 | 101 | 3.15 |
| PBS | — | 32 | 40 | 4.40 |

SUMMARY OF DISCLOSURE

In summary of this disclosure, the present invention provides a novel procedure for the separation and conjugation of HA protein from influenza virus to obtain a potentiated immune response to the HA protein. Modifications are possible within the scope of this invention.

REFERENCE

1. Madoff, D. H. and Lenard, J. (1982) Cell 28:821–828.
2. Neimann, H. and Klenk, H. D. (1981) J. Molecular Biology 153:991–1010.
3. Johnson, D. C. and spear, P. G. (1983) Cell 32:987–997.
4. Veit, M., Schmidt, M. F. G. and Rott, R. (1989) Virology 168:173–176.
5. Hardwick, J. M. et al. (1986) J. Cell Biology 103:829–838.
6. Schmidt, M. f. G. and Schlesinger, M. J. (1979) Cell 17:813–819.
7. Hiller, G. and Weber, K. (1985) J. Virology 55:651–659.
8. Schmidt, M. F. G., Brecha, M. and Schlesinger, M. J. (1979) Proceedings of the National Academy of Science, USA 76:1687–1691.
9. Hancock, J. F. et al. (1989) Cell 57:1167–1177.
10. Jing, S. and Trowbridge, I. S. (1987) EMBO J. 6:327–331.
11. Segrue, R. J., Belshe, R. B., and Hay, A. J. (1990) Virology 179:51–56.

What we claim is:

1. A method of forming a conjugate of a whole hemagglutinin, HA, protein of influenza virus, which comprises the steps of:

isolating the whole HA protein containing transmembrane domain and endodomain from the influenza virus by a method consisting of extracting the whole HA protein from the influenza virus with a non-denaturing detergent.

forming a free sulfhydryl group in the endodomain of the isolated whole HA protein, and cross-linking the free sulfhydryl group in the endodomain of the isolated whole HA protein to a carrier molecule which potentiates an immune response to said HA protein.

2. The method of claim 1 wherein said non-denaturing detergent is octyl-β-glucoside or sodium cholate.

3. The method of claim 1 wherein said step of forming a free sulfhydryl group is effected by contacting the isolated whole HA protein with hydroxylamine.

4. The method of claim 1 wherein said carrier molecule comprises a HA protein and a linker molecule.

5. The method of claim 4 wherein said linker molecule is a bis-maleimide compound.

6. The method of claim 1 wherein said carrier molecule comprises a carrier protein or carbohydrate and a heterobifunctional linker molecule.

7. The method of claim 6 wherein said carrier protein or carbohydrate comprises diphtheria toxoid, tetanus toxoid or influenza NP protein.

8. The method of claim 7 wherein said heterobifunctional linker molecule comprises a maleimide-N-hydroxysuccinimide ester.

9. A method of preparing an immunological composition comprising a conjugate of a whole HA protein of influenza virus, said method comprising the steps of:

forming said conjugate of a whole HA protein of influenza virus according to claim 1, and preparing an immunological composition comprising said conjugate of a whole HA protein.

\* \* \* \* \*